United States Patent [19]

Trostmann et al.

[11] Patent Number: 5,401,875
[45] Date of Patent: Mar. 28, 1995

[54] 2-AMINOCARBOXYLIC ACIDS AND THEIR DERIVATIVES, PROCESSES FOR THEIR PREPARATION AND THEIR USE AS MEDICAMENTS

[75] Inventors: Uwe Trostmann, March-Hugstetten; Johannes Hartenstein, Stegen-Wittental; Claus Rudolph, Vörstetten; Christoph Schächtele, Freiburg; Hartmut Osswald, Emmendingen; Günter Weinheimer, Denzlingen, all of Germany

[73] Assignee: Godecke Aktiengesellschaft, Berlin, Germany

[21] Appl. No.: 681,500
[22] PCT Filed: Oct. 30, 1989
[86] PCT No.: PCT/EP89/01293
§ 371 Date: Apr. 22, 1991
§ 102(e) Date: Apr. 22, 1991
[87] PCT Pub. No.: WO90/05130
PCT Pub. Date: May 17, 1990

[30] Foreign Application Priority Data

Oct. 31, 1988 [DE] Germany ............... 38 36 987.7

[51] Int. Cl.⁶ ............... C07C 229/12; A61K 31/195
[52] U.S. Cl. ............... 562/567; 514/538; 514/547; 514/551; 514/561; 560/170; 562/444
[58] Field of Search ............... 514/551, 561, 538, 547; 560/170; 562/567, 444

[56] References Cited

U.S. PATENT DOCUMENTS

| | | | |
|---|---|---|---|
| 3,647,868 | 3/1972 | Ernst | 260/534 |
| 3,778,268 | 12/1973 | Ushiyama et al. | 96/74 |
| 4,309,327 | 1/1982 | Ishikura et al. | 260/29.6 |
| 4,358,368 | 11/1982 | Hellsten et al. | 209/167 |
| 4,450,173 | 5/1984 | Erhardt et al. | 424/309 |

FOREIGN PATENT DOCUMENTS

| | | |
|---|---|---|
| 0053434 | 10/1981 | European Pat. Off. . |
| 1518362 | 6/1969 | Germany . |
| 727482 | 3/1952 | United Kingdom . |
| 9005130 | 5/1990 | WIPO .................... 562/567 |

OTHER PUBLICATIONS

David Bradshaw et al., "Therapeutic Potential of Protein Kinase C Inhibitors", Agents Actions 38 (1993), pp. 135–147.
Chemical Abstracts, vol. 66, Apr. 10, 1967, pp. 6335, 67040u.
Chemical Abstracts, vol. 104, Jun. 16, 1986, p. 201, 210577k.

Primary Examiner—José G. Dees
Assistant Examiner—B. Frazier
Attorney, Agent, or Firm—Elizabeth M. Anderson

[57] ABSTRACT

The invention concerns 2-aminocarboxylic acids and derivatives of formula

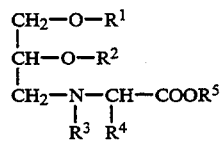

processes for their preparation, as well as medicaments containing them for the inhibition of protein kinase C and thus for the prevention and/or treatment of heart and blood vessel diseases, such as thromboses, arterioscleroses, hypertension, of inflammatory processes, allergies, cancers, and certain degenerative damages of the central nervous system.

15 Claims, No Drawings

2-AMINOCARBOXYLIC ACIDS AND THEIR DERIVATIVES, PROCESSES FOR THEIR PREPARATION AND THEIR USE AS MEDICAMENTS

BACKGROUND OF THE INVENTION

Protein kinase C plays an important role in intracellular signal transduction and is closely connected with the regulation of contractile, secretory, and proliferative processes (Y. Nishizuka, Nature 308:693–698, 1984).

SUMMARY OF THE INVENTION

The invention concerns a compound of formula

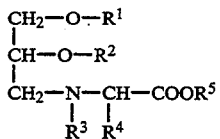
I or a pharmaceutically acceptable salt thereof wherein $R^1$, $R^2$, $R^3$, $R^4$, and $R^5$ are as described below.

Preferred compounds of the instant invention are those wherein $R^1$ is octyl or octadecyl, $R^2$ and $R^3$ are each independently hydrogen or methyl, $R^4$ is hydroxymethyl, hydroxyethyl, hydroxybenzyl, or ethoxycarbonyl, and $R^5$ is hydrogen or ethyl.

More preferred compounds of the instant invention are those named:

2-[N-methyl-N-(3-octadecyloxy-2-hydroxypropyl)]-amino-3-hydroxypropionic acid hydrochloride;

2-[N-methyl-N-(3-octyloxy-2-hydroxypropyl)]-amino-3-hydroxypropionic acid;

2-[N-methyl-N-(3-octadecyloxy-2-hydroxypropyl)]-amino-3-hydroxypropionic acid ethyl ester;

(±)-2-N-(3-octadecyloxy-2-hydroxypropyl)-aminoacetic acid hydrochloride;

2-N-(3-octadecyloxy-2-hydroxypropyl)amino-3-hydroxypropionic acid hydrochloride;

2-N-(3-octadecyloxy-2-methoxypropyl)aminopropionic acid ethyl ester oxalate;

2-N-(3-octadecyloxy-2-methoxypropyl)-amino-3-hydroxybutyric acid;

2-N-(3-octadecyloxy-2-hydroxypropyl)aminomalonic acid diethyl ester;

2-N-(3-octadecyloxy-2-hydroxypropyl)-amino-3-phenylpropionic acid.

The invention also concerns a pharmaceutical composition for the prevention and/or treatment of heart and blood vessel diseases, inflammatory diseases, allergies, cancers, viral diseases, and degenerative diseases of the central nervous system comprising a therapeutically effective amount of a compound according to formula I below wherein $R^4$ is defined as hydrogen, methyl, hydroxyalkyl, benzyl, hydroxybenzyl, carboxyl, or alkoxycarbonyl in combination with a pharmaceutically acceptable carrier.

The invention also concerns methods of treating and methods of preventing heart and blood vessel diseases, inflammatory diseases, allergies, cancers, vital diseases, and degenerative diseases of the central nervous system in a patient suffering therefrom comprising administering to said patient a therapeutically effective amount of a composition as above in unit dosage form.

DETAILED DESCRIPTION

The instant invention concerns new 2-aminocarboxylic acids and derivatives of formula

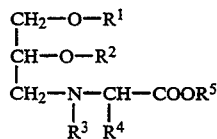
I and the pharmaceutically acceptable salts thereof wherein $R^1$ is a straight-chained or branched, saturated or unsaturated alkyl group of from 1 to 20 carbon atoms, $R^2$ and $R^3$, which may be the same or different, are hydrogen or a straight-chained or branched alkyl group with from 1 to 4 carbon atoms, $R^4$ is hydroxybenzyl, a carboxyl group, a hydroxyalkyl or alkoxycarbonyl group from 1 to 4 carbon atoms each, and $R^5$ is hydrogen or a straight-chained or branched alkyl group with from 1 to 4 carbon atoms.

Preferred compounds of the invention are those of formula I where $R^1$ is octyl- or octadecyl, $R^2$ and $R^3$, which may be the same or different, are hydrogen or methyl, $R^4$ is hydroxymethyl, hydroxyethyl, hydroxybenzyl or ethoxycarbonyl, and $R^5$ is hydrogen or lower alkyl with of from 1 to 4 carbon atoms.

More preferred compounds of the invention are:

2-[N-methyl-N-(3-octadecyloxy-2-hydroxypropyl)]-amino-3-hydroxypropionic acid hydrochloride;

2-[N-methyl-N-(3-octyloxy-2-hydroxypropyl)]-amino-3-hydroxypropionic acid;

2-[N-methyl-N-(3-octadecyloxy-2-hydroxypropyl)]-amino-3-hydroxypropionic acid ethyl ester;

(±)-2-N-(3-octadecyloxy-2-hydroxypropyl)-aminoacetic acid hydrochloride;

2-N-(3-octadecyloxy-2-hydroxypropyl)-amino-3-hydroxypropionic acid hydrochloride;

2-N-(3-octadecyloxy-2-methoxypropyl)-aminopropionic acid ethyl ester oxalate;

2-N-(3-octadecyloxy-2-methoxypropyl)amino-3-hydroxybutyric acid;

2-N-(3-octadecyloxy-2-hydroxypropyl)-aminomalonic acid diethyl ester;

2-N-(3-octadeycyloxy-2-hydroxypropyl)-amino-3-phenylpropionic acid.

The invention also concerns a process for the preparation of 2-aminocarboxylic acids and derivatives thereof, which is characterized in that either a) amino compounds of the formula,

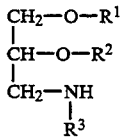
II in which $R^1$, $R^2$, and $R^3$ have the above meanings, are reacted with compounds of formula

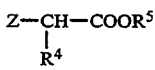
III in which $R^4$ and $R^5$ have the above meanings, Z is a readily removable group such as, e.g., a tosyl group or a halogen atom, to compounds of formula I, or (b) that one reacts, epoxides of formula

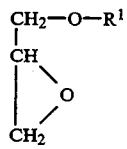
                      IV in which $R^1$ has the above meaning, with compounds of the formula

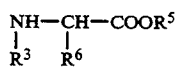
                      V in which $R^3$ and $R^5$ have the above meanings and $R^6$ is hydrogen, methyl, benzyl or carboxyl or a group of formulae VI or VIa,

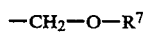
                      VI or

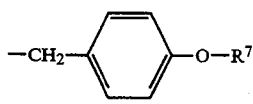
                      VIa in which $R^7$ is a protective group which is easily split off, such as, e.g., benzyl, chlorobenzyl, 2,6-dichlorobenzyl or tert.-butyl, to compounds of formula

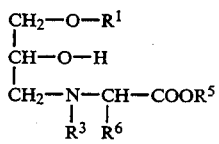
                      VII in which $R^1$, $R^3$, $R^5$, and $R^6$ have the above meanings. For the case in which $R^2$ is not hydrogen, the compounds are alkylated according to known processes to produce compounds of formula

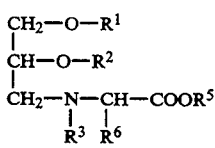
                      VIII in which $R^1$, $R^2$, $R^3$, $R^5$ and $R^6$ possess the above meanings, and subsequently converting these compounds of formula VIII by hydrogenolytic or acid splitting off of the above-mentioned protective groups into compounds of formula I.

The amino ethers serve as starting compounds in the process of making compounds of formula

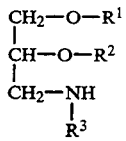
                      II in which $R^1$, $R^2$ and $R^3$ the above meanings and $R^2$ is not hydrogen. They are prepared by either:

1) for the case in which $R^2$ is methyl or ethyl, reacts the salts of the amino alcohols of formula

                      IX in which $R^1$ and $R^3$ possess the above meanings, with trialkoxonium tetrafluoroborate, or 2) converts compounds of the formula

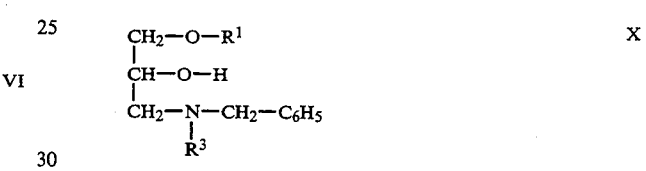
                      X in which $R^1$ and $R^3$ possess the above meanings and $R^3$ can also be a benzyl group, into the sodium alcoholates and reacts these with compounds of formula $$Y-R^2 \quad\quad XI$$

in which $R^2$ has the above meaning and Y represents a readily removable group, such as, e.g., a tosyl radical or a halogen atom, to compounds of formula

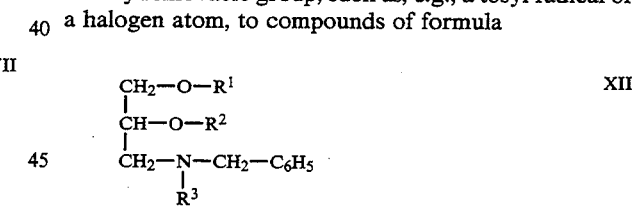
                      XII in which $R^1$, $R^2$, and $R^3$ have the above meanings, and subsequently converts compounds of formula XII with hydrogen in the presence of palladium into compounds of formula II, in which $R^1$, $R^2$, and $R^3$ have the above meanings.

The preparation of compounds of formula IX is described in U.S. Pat. No. 4,855,489. The derivatives of the aminocarboxylic acid esters of formula V used for this process are either commercially available or can be prepared according to generally known processes (Houben-Weyl Vol. XI/2, p. 308 et seq.).

Compounds of structure I, in which $R^1$ is a straight-chained alkyl group with from 1 to 18 carbon atoms, $R^2$ hydrogen, $R^3$ and $R^4$ hydrogen or a lower alkyl and $R^5$ hydrogen, are known and, on the basis of their properties, suitable for dermatological and cosmetic preparations (DE-A 1518362) and as surface active compounds (DD-60382; Fette, Seifen, Anstrichmittel 68, 964 (1966)). An action upon protein kinase C has hitherto not been described.

The reaction of the amino alcohols of formula IX to amino ethers of formula II can be carried out either in that one reacts the hydrochlorides of the amino alcohols IX with an excess of trialkyl oxonium tetrafluoroborate in aprotic solvents, such as e.g. tetrahydrofuran or ether, but preferably dichloromethane, at temperatures between 0° and 25° C., preferably at the boiling temperature of the corresponding solvent, or in that one reacts the amino alcohols of formula X with sodium hydride in aprotic solvents, such as tetrahydrofuran or diethyl ether but preferably N,N-dimethylformamide, at temperatures between 10° and 50° C., preferably at room temperature, and subsequently reacts with compounds of formula XI in the same solvent at temperatures between 20° and 50° C., preferably at the boiling point of the solvent. The reaction products can be isolated and purified with known separation processes, such as crystallization and/or chromatography.

The possibly necessary catalytic hydrogenation of N-benzyl or N,N-dibenzyl compounds of formula XII is carried out by dissolving the corresponding educts in polar solvents, such as methanol or ethanol, and saturates with hydrogen, preferably at atmospheric pressure and room temperature, in the presence of Pd/C as catalyst. The process of making products of formula II takes place by crystallization of the corresponding salts, preferably of the hydrochlorides.

The reaction of the compounds of formula II with compounds of formula III takes place in that one allows the starting products to react in a polar or apolar solvent, such as isopropanol, N,N-dimethylformamide or toluene but preferably ethanol, at temperatures between 20° and 80° C., preferably at the boiling point of the solvent, in the presence of inorganic or organic bases, such as, for example sodium carbonate, piperidine or pyridine, but preferably potassium carbonate. In general, the reaction time is between 1 and 24 hours but preferably is about 10 hours. The purification of the products of the formula I takes place by crystallization and/or chromatography.

The preparation of compounds of formula VII takes place by reacting by known methods in U.S. Pat. No. 4,208,345 (Seifen, Fette, Anstrichmittel 68, 964 (1966)) epoxides of formula IV with aminocarboxylic acid derivatives of formula V, in which $R^5$ is a $C_{1-4}$ alkyl group, in an organic solvent and/or water but preferably in ethanol at temperatures between 20° and 100° C. but preferably at 50° C. If, for this reaction, aminocarboxylic acids are used of formula V ($R^5$=H), then the presence of an inorganic base, preferably sodium hydroxide, is necessary.

Compounds of formula VII are O-alkylated by converting these compounds into the sodium alcoholates and then reacting in the same solvent, such as tetrahydrofuran or N,N-dimethylformamide, with alkyl compounds of formula XI at temperatures between 25° and 100° C. but preferably at the boiling point of the solvent.

The possibly necessary splitting off of a protective group $R^7$ from compounds of formula VIII, in which $R^6$ is a chemical group of formula VI, is carried out either a) by means of catalytic hydrogenation of O-benzyl compounds of formula VIII in polar solvents, such as methanol, ethanol, acetic acid or water, but preferably in mixtures of methanol/acetic acid/water 9:1:1, with hydrogen in the presence of Pd/C as catalyst or b) by reaction of the O-tert.-butyl compounds of formula VIII with strong acids, such as hydrobromic acid or hydrochloric acid and preferably with trifluoroacetic acid, in solvents, such as ethanol, water, acetic acid, dichloromethane or also in reagent as solvent, at temperatures between 0° and 50° C. but preferably at room temperature. The obtaining of the products takes place by chromatography and/or crystallization.

Since the compounds of formula I have chiral centers, they are present either as diastereomer mixture, racemic mixtures or in the form of enantiomers.

For the purpose of purification and for galenic reasons, the compounds of the formula I are preferably converted into crystalline, pharmacologically acceptable salts. The salts are obtained in the usual way by neutralization of the bases with corresponding inorganic or organic acids. Possible acids are hydrochloric acid, sulphuric acid, phosphoric acid, hydrobromic acid, acetic acid, tartaric acid, lactic acid, citric acid, malic acid, salicylic acid, ascorbic acid, malonic acid, fumaric acid, oxalic acid or succinic acid. As a rule, the acid-addition salts are obtained by known methods by mixing of the free bases or of their solutions in water or an organic solvent, for example a lower alcohol, such as methanol, ethanol or propan-2-ol, or a lower ketone, such as acetone or butan-2-one, or an ether, such as diethyl ether, diisopropyl ether, tetrahydrofuran or dioxan.

The compounds according to the invention of formula I display interesting pharmacological properties. They represent a group of substances which inhibit protein kinase C. The advantage of these compounds in comparison with the compounds described in the EP A-0255126 (Example 6 in Table 1) and U.S. Pat. No. 4,173,641 (Example 7) is that they inhibit protein kinase C with higher potency, whereas cyclo AMP-dependent kinase, cyclo GMP-dependent kinase and myosine light chain kinase are far less influenced (see Table 1).

Since protein kinase C plays a key role in intracellular signal transduction and is closely connected with the regulation of contractile, secretory and proliferative processes (Y. Nishizuka, *Nature* 308:693–698/1984), the compounds of the invention can be used for the treatment and/or prevention of heart and blood vessel diseases, such as thromboses, arterioscleroses, hypertension, of inflammatory processes, allergies, cancers, viral diseases and certain degenerative damages of the central nervous system.

The compounds of the invention, formula I, can be administered orally or parenterally in liquid or solid form. As injection solution thereof preferably uses water which contains the additives usual for injection solutions, such as stabilizing agents, solubilizing agents and/or buffers.

Such additives are, e.g., tartrate and citrate buffers, ethanol, complex formers (such as ethylene-diamine-tetraacetic acid and its non-toxic salts), as well as high molecular polymers (such as liquid polyethylene oxide) for viscosity regulation. Solid carrier materials are, e.g., starch, lactose, mannitol, methyl cellulose, talc, highly dispersed silicic acids, high molecular fatty acids (such as stearic acid), gelatin, agar-agar, calcium phosphate, magnesium stearate, animal and vegetable fats, solid high molecular polymers (such as polyethylene glycol); compositions suitable for oral administration can, if desired, additionally contain flavoring and/or sweetening agents.

The following comparative experiments show the pharmacological effectiveness of the compounds of the invention of formula I:

1. C-kinase

The enzyme is purified from rat brain or smooth muscle (chicken stomach). Its activity is determined via the incorporation of phosphorus-32 labelled phosphate in histone. The reaction batch of 200 μL contains the following components: 50 mM HEPES-NaOH, pH 7.5, 5 mM MgCl$_2$, 1 mM DTT, 4 μM free Ca$^{2+}$, 10 μM ATP, 1 μg phosphatidylserine, 0.2 μg 1,2-diolein, as well as 40 μg histone H-1. The batch is preincubated for 4 minutes at 30° C. and the reaction then started by addition of 5 nM PKC. After 5 minutes incubation at 30° C. the reaction is stopped with 10% TCA and the samples then filtered off. The phosphate incorporation is determined by means of Cerenkov counting in a scintillation counter.

2. A-kinase

The measurement of the activity takes place with the commercially available catalytic subunit of the enzyme. The incorporation of phosphorus-32 labelled phosphate into histone is thereby measured. The reaction batch of 200 μL contains the following components: 50 mM PIPES-NaOH, pH 7.5, 10 mM MgCl$_2$, 1 mM DTT, 40 μM ATP, as well as 50 μg histone-H-2B. The carrying out of the test takes place as in the case of C-kinase.

3. G-kinase

The enzyme was purified from bovine lung and its activity determined via the incorporation of phosphorus 32-labelled phosphate into histone. In the test batch are contained the following components: 20 mM Tris-HCl, pH 7.4, 5 mM MgCl$_2$, 1 mM DTT, 10 μM ATP, 10 μM cGMP, 40 μg BSA, 2% glycerol, as well as 10 μg histone II-A. The starting of the reaction takes place by addition of 2.5 nM G-kinase. Otherwise, the carrying out of the test takes place as in the case of C-kinase.

4. MLC-kinase

Not only the enzyme but also the substrate (MLC) are purified from chicken stomach. The activity measurement also takes place via the incorporation of phosphorus-32 labelled phosphate. The reaction batch of 200 μL contains the following components: 50 mM MOPS-NaOH, pH 7.2, 5 mM MgCl$_2$, 100 μM CaCl$_2$, 100 nM calmodulin, 1 mM DTT, 250 μM ATP, as well as 25 μM MLC. The reaction is started by addition of about 1 nM MLC kinase; otherwise, the carrying out of the test takes place as in the case of C-kinase.

The results of the comparative experiments are shown in Table 1.

TABLE 1

| Ex-ample | Inhibition of [IC$_{50}$-values (Mole/L)] | | | |
|---|---|---|---|---|
| | PKC | cAMP-kinase | cGMP-kinase | MLC-kinase |
| 1 | $2.5 \times 10^{-6}$ | $>1 \times 10^{-4}$ | $>1 \times 10^{-4}$ | $>1 \times 10^{-4}$ |
| A | $5.0 \times 10^{-6}$ | $>1 \times 10^{-4}$ | $>1 \times 10^{-4}$ | $>1 \times 10^{-4}$ |
| B | $7.0 \times 10^{-6}$ | $2.9 \times 10^{-5}$ | $2.8 \times 10^{-5}$ | $5.1 \times 10^{-6}$ |

A: (±)-1-dimethylamino-3-octadecyloxy-2-propyl acetate hydrochloride (EP 0255126)
B: 4-aminomethyl-1-[2,3-(di-n-decyloxy)-n-propyl]-4-phenylpiperidine (US 4173641)
PKC: protein kinase C
cAMP-kinase: cyclo-AMP-dependent kinase
cGMP-kinase: cyclo-GMP-dependent kinase
MLC-kinase: myosine light chain kinase The following examples are illustrative of the invention but are not intended to limit its scope.

EXAMPLE 1

2-[N-Methyl-N-(3-octadecyloxy-2-hydroxypropyl)]-amino-3-hydroxypropionic acid hydrochloride A reaction mixture of 2.0 g (5.1 mMole) (±)-3-methylamino-1-octadecyloxy-2-propanol and 0.93 g (5,1 mMole) 2-bromo-3-hydroxypropionic acid ethyl ester, together with 2.1 g (15.3 mMole) potassium carbonate in 60 mL anhydrous ethanol, is heated under reflux for 4 hours. After this time, 0.9 g (5.1 mMole) bromo-hydrin and 21 g (15.3 mMole) potassium carbonate are again added thereto and heated to reflux for a further hour. One subsequently allows this to cool to room temperature, filters and distills off the solvent in a vacuum. One takes up the residue in 100 mL dichloromethane and adds methanol thereto up to complete solution. Subsequently, one adds 30 mL 2N hydrochloric acid thereto and stirs up vigorously for 15 minutes, then separates the organic phase, dries it over sodium sulphate and distills the solvent therefrom in a vacuum. The residue crystallizes from diethyl ether; m.p. 100° to 104° C.

In an analogous manner the following is prepared:
2-[N-methyl-N-(3-octyloxy-2-hydroxypropyl)]-amino-3-hydroxypropionic acid (1.a); m.p. 177° C. (decomp.).

EXAMPLE 2

2-[N-Methyl-N-(3-octadecyloxy-2-hydroxypropyl)]-amino-3-hydroxypropionic acid ethyl ester A reaction mixture of 300 mg (0.7 mMole) (±)-3-methylamino-1-octadecyloxy-2-propanol and 180 mg (0.7 mMole) 2-bromo-3-hydroxypropionic acid ethyl ester, together with 210 mg (1.4 mMole) potassium carbonate, is heated under reflux for 3 hours in 10 mL anhydrous ethanol. The cooled reaction solution is filtered, freed from solvent in a vacuum and taken up in 50 mL dichloromethane. One filters from insolubles and separates the product mixture column chromatographically (silica gel, dichloromethane/methanol 18:1). The product is isolated with the first fraction; m.p. 54° to 58° C. (from pentane).

EXAMPLE 3

(±)-2-N-(3-Octadecyloxy-2-hydroxypropyl)-aminoacetic acid hydrochloride

Into a solution of 660 mg (2 mMole) (±)-1-octadecyloxy-2,3-epoxypropane in 10 mL ethanol one adds at room temperature 610 mg (8.1 mMole) glycine and subsequently adds thereto 120 mg (3 mMole) sodium hydroxide, dissolved in 10 mL water. One heats the reaction mixture for 1 hour to 80° C., allows to cool to room temperature, adds thereto 20 mL 2N hydrochloric acid and 100 mL dichloromethane, stirs up vigorously, separates the organic phase and dries it over sodium sulphate. After distilling off the solvent in a vacuum, the residue is recrystallized from ether. After suction filtration and drying of the crystals in a vacuum, the product is isolated; m.p. 65° to 72° C.

In an analogous manner the following are prepared:
2-N-(3-octadecyloxy-2-hydroxypropyl)amino-3-phenyl-propionic acid (3.a); m.p. 47° to 50° C.;
2-N-(3-octadecyloxy-2-hydroxypropyl)amino-3-(4-hydroxy)phenyl-propionic acid hydrochloride (3.b); m.p. 182° to 183° C.;
diethyl-2-N-(3-octadecyloxy-2-hydroxypropyl)amino-malonate oxalate (3.c); m.p. 130° to 132° C.

EXAMPLE 4

2-N-(3-Octadecyloxy-2-hydroxypropyl)-amino-3-hydroxypropionic acid hydrochloride 640 mg (1.2 mMole) 2-N-(3-octadecyloxy-2-hydroxypropyl)-amino-3-tert.-butyloxypropionic acid hydrochloride in 15 mL trifluoroacetic acid are stirred for 1 hour at room temperature. One then distills off the reagent in a vacuum, takes up the residue in 50 mL dichloromethane, adds thereto 20 mL of a saturated solution of sodium hydrogen carbonate in water and stirs for 15 minutes at room temperature. One filters off the resultant precipitate with suction, dissolves it in methanol, adds thereto 20 mL 2N hydrochloric acid and, after 5 min stirring, distills off the solvent. The organic phase is separated from the mother liquor, acidified with 2N hydrochloric acid, the resultant precipitate is dissolved by the addition of methanol, the organic phase separated, the aqueous phase again extracted with dichloromethane, the combined organic phases dried over sodium sulphate and the product, after distilling off of the solvent in a vacuum, together with the above-isolated precipitate, produced from ether. The pure product is isolated after suction filtration; m.p. 62° to 67° C.

The 2-N-(3-octadecyloxy-2-hydroxypropyl)-amino-3-tert.-butyloxypropionic acid hydrochloride used as precursor is prepared as follows:

In a solution of 125 mg (3.1 mMole) sodium hydroxide in 20 mL ethanol are dissolved 0.5 g (3.1 mMole) L-O-tert.-butylserine and subsequently 1 g (3.1 mMole) (±)-1-octadecyloxy-2,3-epoxypropane added thereto. After the addition of 10 mL water, the reaction mixture is heated for 4 hours to 80° C. Subsequently, 50 mL water and 100 mL dichloromethane are added thereto and the mixture is acidified with 2N hydrochloric acid. One separates the organic phase, extracts the aqueous phase a further three times with, in each case, 30 mL dichloromethane, dries the combined organic extracts over sodium sulphate and, after distilling off of the solvent in a vacuum, separates the residue column chromatographically (silica gel, dichloromethane/methanol 9:1), The product is isolated with the fourth fraction.

EXAMPLE 5

2-N-(3-Octadecyloxy-2-methoxypropyl)-aminopropionic acid ethyl ester oxalate

A reaction mixture of 390 mg (1 mMole) (±)-3-amino-2-methoxy-1-octadecyloxypropane, 180 mg (1 mMole) 2-bromopropionic acid ethyl ester and 300 mg (2.2 mMole) potassium carbonate in 20 mL anhydrous ethanol is heated under reflux for 3 hours. Subsequently, one again adds thereto 540 mg (2 mMole) 2-bromopropionic acid ethyl ester and 600 mg (4.4 mMole) potassium carbonate and further heats under reflux for 4 hours. The cooled solution is then filtered, the solvent is distilled off therefrom in a vacuum and the residue separated column chromatographically (silica gel, dichloromethane/methanol 36:1). The product is isolated with the first fraction. The amino acid ester is subsequently mixed in 10 mL ether with 36 mg oxalic acid, the solvent is distilled off therefrom in a vacuum and the residue brought to crystallization from ether/cyclohexane; m.p. 77° to 80° C.

The (±)-3-amino-2-methoxy-1-octadecyloxypropane hydrochloride used as precursor is prepared as follows:

1.6 g (4 mMole) (±)-3-amino-1-octadecyloxy-2-propanol hydrochloride, together with 3.12 g (20.0 mMole) trimethyloxonium tetrafluoroborate in 50 mL dichloromethane, are heated to reflux over 24 hours. The cooled reaction solution is diluted with 150 mL dichloromethane and carefully mixed with 20 mL 2N aqueous sodium hydroxide solution. One stirs up vigorously, separates the organic phase, mixes it with 30 mL 2N hydrochloric acid and again stirs up vigorously. After separation of the organic phase, drying over sodium sulphate and distilling off of the solvent, the product is isolated.

In an analogous way the following is prepared:
2-N-(3-octadecyloxy-2-methoxypropyl)-amino-3-hydroxybutyric acid (5.a); m.p. 48° to 60° C.

EXAMPLE 6

2-[N-Methyl-N-(2-methoxypropyl-3-octadecyloxy)-]amino-3-hydroxy-propionic acid hydrochloride A mixture of 0.41 g (1 mMole) 1-methylamino-2-methoxy-3-octa-decyloxypropan hydrochloride, 0.20 g (1 mMole) ethyl-2-bromo-3-hydroxy-propionate and 0.41 g (3 mMole) potassium carbonate in 30 mL absolute ethanol is boiled under reflux for 4 hours. Then additional 0.2 g (1 mMole) bromohydrin and 0.27 g (2 mMole) potassium carbonate are added. The mixture is boiled again for 6 hours and subsequently filtered hot. The filtrate is evaporated, diluted in dichloromethane, and a few methanol aufgenommen, 30 mL 2N hydrochloric acid are added and stirred for 15 minutes at ambient temperature. The organic phase is separated and the aqueous phase extracted three times with dichloromethane. The combined organic extracts are dried over sodium sulphate and the solvent distilled in a vacuum. The residue is treated with ether and subsequently with warm acetone; m.p. 63° to 65° C.

(±)-1-Methylamino-2-methoxy-3-octadecyloxypropan hydrochloride used as starting material is prepared as follows:

A reaction mixture of 3.49 g (8.86 mMole) 1-methylamino-3-octadecyloxypropan-2-ol and 6.5 g (44.6 mMole) trimethyloxonium-tetrafluoroborate in 60 mL dichloromethane is heated under reflux for 24 hours. Subsequently one dilutes with 100 mL dichloromethane, adds carefully 20 mL 2N sodium hydroxide, separates the organic phase, adds to this 50 mL 2N hydrochloric acid, stirs heavily for 10 minutes and separates the organic phase. After drying and distilling off the solvent in a vacuum the residue is stirred out from n-pentane.

We claim:
1. A compound of formula

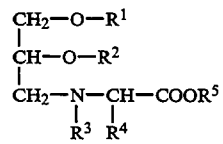

I or a pharmaceutically acceptable salt thereof wherein:
$R^1$ is a straight or branched, saturated or unsaturated alkyl of from 1 to 20 carbon atoms,
$R^2$ and $R^3$ are each independently hydrogen or a straight or branched alkyl of from 1 to 4 carbon atoms,
$R^4$ is benzyl, hydroxybenzyl, carboxyl, hydroxyalkyl, or alkoxycarbonyl wherein there are form 1 to 4 carbon atoms in the alkyl or alkoxy group; and
$R^5$ is hydrogen or a straight or branched alkyl of from 1 to 4 carbon atoms.

2. A compound according to claim 1 wherein
$R^1$ is octyl or octadecyl,
$R^2$ and $R^3$ are each independently hydrogen or methyl, R⁴ is hydroxyethyl, hydroxybenzyl, or ethoxycarbonyl, and R⁵ is hydrogen or ethyl.

3. A compound named 2-[N-methyl-N-(3-octadecyloxy-2-hydroxypropyl)]-amino-3-hydroxypropionic acid hydrochloride.

4. A compound named 2-[N-methyl-N-(3-octyloxy-2-hydroxypropyl)]-amino-3-hydroxypropionic acid.

5. A compound named 2-[N-methyl-N-(3-octadecyloxy-2-hydroxypropyl)]-amino-3-hydroxypropionic acid ethyl ester.

6. A compound named (±)-2-N-(3-octadecyloxy-2-hydroxypropyl)-aminoacetic acid hydrochloride.

7. A compound named 2-N-(3-octadecyloxy-2-hydroxypropyl)-amino-3-hydroxypropionic acid hydrochloride.

8. A compound named 2-N-(3-octadecyloxy-2-methoxypropyl)-aminopropionic acid ethyl ester oxalate.

9. A compound named 2-N-(3-octadecyloxy-2-methoxypropyl)-amino-3-hydroxybutyric acid.

10. A compound named 2-N-(octadecyloxy-2-hydroxypropyl)-aminomalonic acid diethyl ester.

11. A compound named 2-N-(3-octadecyloxy-2-hydroxypropyl)-amino-3-phenyl-propionic acid.

12. A pharmaceutical composition for the inhibition of a kinase selected from the group consisting of protein kinase C, cyclo-AMP-dependent kinase, cyclo-GMP-dependent kinase, and myosine light chain kinase comprising a therapeutically effective inhibiting amount of a compound of formula

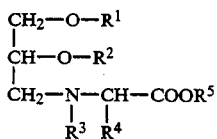

or a pharmaceutically acceptable salt thereof wherein:

R¹ is a straight or branched, saturated or unsaturated alkyl of from 1 to 20 carbon atoms, R² and R³ are each independently hydrogen or a straight or branched alkyl of from 1 to 4 carbon atoms, R⁴ is hydrogen, methyl, benzyl, hydroxybenzyl, carboxyl, hydroxyalkyl, or alkoxycarbonyl, and R⁵ is hydrogen or a straight or branched alkyl of from 1 to 4 carbon atoms in combination with a pharmaceutically acceptable carrier.

13. The composition of claim 12 wherein the kinase is protein kinase C.

14. A method of inhibiting a kinase selected from the group consisting of protein kinase C, cyclo-AMP-dependent kinase, cyclo-GMP-dependent kinase, and myosine light chain kinase in a patient suffering therefrom comprising administering to said patient a therapeutically effective inhibiting amount of a compound of formula

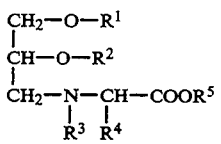

or a pharmaceutically acceptable salt thereof wherein:

R¹ is a straight or branched, saturated or unsaturated alkyl of from 1 to 20 carbon atoms, R² and R³ are each independently hydrogen or a straight or branched alkyl of from 1 to 4 carbon atoms, R⁴ is hydrogen, methyl, benzyl, hydroxybenzyl, carboxyl, hydroxyalkyl, or alkoxycarbonyl, and R⁵ is hydrogen or a straight or branched alkyl of from 1 to 4 carbon atoms in combination with a pharmaceutically acceptable carrier.

15. The method of claim 14 wherein the kinase is protein kinase C.

* * * * *